US006986886B2

(12) United States Patent
Hammond et al.

(10) Patent No.: US 6,986,886 B2
(45) Date of Patent: Jan. 17, 2006

(54) HAIR CONDITIONING COMPOSITIONS AND THEIR USE IN HAIR COLORING COMPOSITIONS

(75) Inventors: Roger Clive Hammond, Staines (GB); Nicholas William Geary, Blue Ash, OH (US); Stevan David Jones, Guildford (GB)

(73) Assignee: The Procter & Gamble Company, Cincinnati, OH (US)

( * ) Notice: Subject to any disclaimer, the term of this patent is extended or adjusted under 35 U.S.C. 154(b) by 23 days.

(21) Appl. No.: 10/460,068

(22) Filed: Jun. 12, 2003

(65) Prior Publication Data

US 2003/0219399 A1 Nov. 27, 2003

Related U.S. Application Data

(63) Continuation of application No. PCT/US01/48600, filed on Dec. 7, 2001.

(30) Foreign Application Priority Data

Dec. 13, 2000 (GB) .............................. 0030369
Aug. 16, 2001 (GB) ............................ 0120048

(51) Int. Cl.
*A61K 7/075* (2006.01)

(52) U.S. Cl. .................. 424/70.12; 424/70.1; 424/70.6
(58) Field of Classification Search ............... 424/70.1, 424/70.6, 70.12
See application file for complete search history.

(56) References Cited

U.S. PATENT DOCUMENTS

| 4,563,347 | A | | 1/1986 | Starch |
| 4,698,065 | A | | 10/1987 | Hoeffkes et al. |
| 4,874,604 | A | | 10/1989 | Sramek |
| 5,078,748 | A | | 1/1992 | Akram et al. |
| 5,114,428 | A | | 5/1992 | Hoeffkes |
| 5,230,710 | A | | 7/1993 | Akran |
| 5,409,695 | A | * | 4/1995 | Abrutyn et al. .......... 424/70.12 |
| 5,613,985 | A | | 3/1997 | Bauer |
| 5,747,435 | A | | 5/1998 | Patel |
| 5,756,436 | A | | 5/1998 | Royce |
| 5,804,171 | A | | 9/1998 | Audousset |
| 6,306,181 | B1 | * | 10/2001 | Terranova et al. ............. 8/409 |

FOREIGN PATENT DOCUMENTS

| EP | 0275707 B1 | 5/1992 |
| GB | 2186889 A | 8/1987 |
| JP | 09040533 A | 10/1997 |
| JP | 2899720 B2 | 6/1999 |
| WO | WO-99/29285 | 6/1999 |
| WO | WO-99/49836 A1 | 10/1999 |
| WO | WO 99/62467 A1 | 12/1999 |
| WO | WO-00/07550 A1 | 2/2000 |
| WO | WO-02/47632 A2 | 6/2002 |
| WO | WO-02/076412 A2 | 10/2002 |

* cited by examiner

*Primary Examiner*—Jyothsna Venkat
(74) *Attorney, Agent, or Firm*—Michael J. Sambrook; Brian M. Bolam; Tara M. Rosnell

(57) ABSTRACT

The present invention relates to a hair care composition comprising a aminofunctional polysiloxane having a specified average effective particle size which provides improved durable conditioning particularly when utilised in conjunction with a hair coloring composition.

16 Claims, No Drawings

HAIR CONDITIONING COMPOSITIONS AND THEIR USE IN HAIR COLORING COMPOSITIONS

CROSS REFERENCE TO RELATED APPLICATION

The application is a continuation of International application PCT/US01/48600 filed on Dec. 7, 2001.

TECHNICAL FIELD OF THE INVENTION

The present invention relates to hair conditioning compositions and in particular hair colouring compositions comprising hair conditioning agents.

BACKGROUND OF THE INVENTION

The alteration of the colour of hair by the application of hair dyes is well known.

In order to provide the consumer with the hair colour and intensity of shade desired, a very complex chemical process is utilised. The hair dyeing molecules are typically produced from the reaction of at least one oxidative colouring agent with an oxidising agent which are formed in situ on the hair of consumers and typically in an aggressive environment at ca pH 10 and in the presence of alkalising agent. Moreover this process is repeated regularly by the consumer in order maintain the desired hair colour and intensity of the hair colour shade and ensure continual, even coverage of the hair including coverage of new hair growth.

The manufacturer of such products is also required to work within a large number of constraints. Since these products are being placed in direct contact with the consumers' skin and potentially accidental contact with the eye or ingestion (for example) can occur during the dyeing process, the formulation must meet rigorous safety requirements and not cause any allergic reaction. In addition to meeting these requirements, the products must also be optically and olfactory pleasing to the consumer and meet certain physical parameters in order to ensure that the product can be easily applied to the hair by the consumer to provide the desired effect, without unintentional staining on the consumers clothes, skin or other objects.

The chemistry involved in the hair dyeing process may result in some damage to the hair which is permanent. Damaging effects include tangling, brittleness and dryness. Consequently there is a need to provide the hair dye composition or hair dyeing kit with a conditioning component in order to combat this damage and improve at least the consumers' perception of the condition of the hair; immediately after the hair dyeing process and the on-going condition of the hair during the post dyeing washing cycle until the next hair dyeing cycle.

The use of conditioning compositions is well known in the art and are incorporated as part of conventional shampoo and conditioning regimes as well as in so called two-in-one shampoo conditioners. Their use in hair dyeing kits is also well known. Typically they are provided in a sachet for use in the final rinse, after dyeing is completed. These conditioners such as amino silicones as described for example in U.S. Pat. No. 4,563,347, EP 275 707 and WO99/49836 usually provide an acceptable immediate improved feel of the hair to the consumer. However, this conditioning benefit is not durable over a number of hair washing cycles such that the consumer becomes dissatisfied with the condition of the hair during the course of the post dyeing cycle.

Unfortunately durable conditioning cannot be achieved by simply increasing the levels of conditioning material in the composition. In fact, if excessive conditioner is applied, the initial feel of the hair becomes heavy and greasy which is completely unacceptable to the consumer.

Moreover if the conditioning material is such that it is sustained on the hair during the post dyeing wash cycle such that it is still present on the hair at the start of the next colouring cycle, the performance of the dyeing process cannot be predicted and may be detrimentally effected. Such a result is equally undesirable for the consumer.

Progress has however been made in the field of durable hair conditioning materials and in particular compounds such as amodimethicone have been identified as delivering improved durable conditioning benefits.

It has further been taught in the art for example in WO99/49836 to utilise microemulsions of organosiloxanes in order to improve the conditioning effect.

However, there is still a need to provide durable conditioning materials for use in hair dye compositions which have the required initial deposition and retention over time without any greasy feel negatives after the initial application and which do not negatively affect the performance of the next hair dyeing cycle.

There is also a need to provide a hair dye composition which does not necessarily require a separate post hair dyeing conditioning step.

SUMMARY OF THE INVENTION

The present invention relates to a hair care composition comprising an amino functional polysiloxane as defined hereinafter having an average particle size of from greater than 2 micrometers to 50 micrometers which provides improved conditioning particularly when utilised in combination with a hair colouring composition.

DETAILED DESCRIPTION OF THE INVENTION

As used herein the hair treated may be "living" i.e. on a living body or may be 'non-living' i.e. in a wig, hairpiece or other aggregation of non-living fibres, such as those used in textiles and fabrics. Mammalian, preferably human hair is preferred. However wool, fur and other melanin containing fibres are suitable substrates for the compositions according to the present invention.

The hair care composition according to the present invention comprises at least one or a mixture of an amino functional polysiloxane compound having the formula:

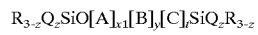

wherein; A represents $R_2SiO$, B represents RQSiO and C represents $R_{3-z}Q_z[A]_{x2}SiOR^1$, wherein R is an alkyl group of 1 to 5 carbons wherein at least 50% of said R groups are methyl, preferably R is a methyl, ethyl, propyl, isopropyl, butyl or isobutyl, a phenyl group, an alkoxy group or an hydroxy group and $R^1$ is R or Q or $R^2$,$R^2$ is $R_{3-z}Q_z[A]_{x3}$ wherein, Q is an amine functional group of the formula —$R^3Z$, $R^3$ is a divalent alkylene radical of 3 to 6 carbons, preferably trimethylene, pentamethylene, —$CH_2CHCH_3CH_2$—, or —$CH_2CH_2CHCH_3CH_2$—, Z is —$N(R^4)_2$, —$NR^4(CH_2)_nN(R^4)_2$, —$N^+(R^4)_3A^-$, —$NR^4(CH_2)_nN^+(R^4)_3A^-$, preferably a monovalent radical including at least 1 amine; unsubstituted amine radical —$NH_2$, alkyl substituted amine radicals such as —$NHCH_3$ or —$NHCH_2CH_2CH_2CH_3$; aminoalkyl substituted amine radicals such as —$NHCH_2CH_2NH_2$, —$NH(CH_2)_6NH_2$ and —$NHCH_2CH_2N(CH_3)_2$; diaminoalkyl substituted amine radicals such as —N(CH$_2$CH$_2$CH$_2$NH$_2$)$_2$—N(CH$_2$CH$_2$CH$_2$N(CH$_3$)$_2$)$_2$, R$^4$ is an H atom or alkyl group of 1 to 20 carbon atoms or phenyl or benzyl, A$^-$ is F$^-$, Cl$^-$, Br$^-$, I$^-$, and wherein: t is from 0 to 3, x$_1$ is from 1 to 3000, x$_2$ is from 0 to 3000, x$_3$ is from 0 to 3000, x$_1$+x$_2$+x$_3$ is from 10 to 3000, y is from 0 to 100, preferably y is 0 when z=1 and preferably y is from 1 to 100 when z=0, z is from 0 to 1, and n is from 2 to 6.

More preferably R is a methyl or hydroxy or methoxy group, most preferably methyl and at least 50% of R groups are methyl. R$^1$ is R or Q, most preferably R, Q is an amine functional group of the formula —R$^3$Z, R$^3$ is propyl or isobutyl and Z is NH$_2$ or NHCH$_2$CH$_2$NH$_2$ and wherein t is from 0 to 2, most preferably 0, x$_1$ is from 10 to 400, x$_2$ is from 22 to 124, x$_1$+x$_2$ is from 10 to 400, y is from 0 to 9 when z=1, and y is from 1 to 9 when z=0.

It has now been found that the particle size of the aminofunctional polysiloxane in the hair care composition plays a critical role in the performance of the composition, particularly when utilised as part of a hair dyeing regime. Accordingly it has now been surprisingly found that compositions comprising aminofunctional polysiloxanes according to the formula described herein above, having an average effective particle size of from greater than 2 micrometers to 50 micrometers, preferably from 5 micrometers to 40 micrometers, more preferably from 10 micrometers to 30 micrometers, most preferably from 15 micrometers to 20 micrometers provides a hair care conditioning composition which not only provides the desired initial conditioning as determined by the Combing technical test Methods and the Sensory Technical Test Method described hereinafter but which is also maintained over a number of hair washing cycles.

The term average effective particle size as used herein refers to the average size of individual discrete particles of amino functional polysiloxanes as defined herein and discrete particles comprising an aminofunctional polysiloxane and a polycation or cationic polymers. Whilst not being bound by theory such particles have been referred to as coascervates and form discrete particles consisting localised concentrations of the amino functionalised silicone that are associated with the hydrophobic environment of the polycation or cationic polymers. Examples of suitable cationic polymers include cationic cellulose (polyquaternium 10) and hydrophobically modified cationic cellulose (i.e. Amerchol's quatrisoft LM200), cationic guar (guar hydroxypropyltrimonium chloride), merquat 100 (polyquaternium 6), Merquat 550 (polyquaternium 7), Luviquat (polyquaternium-16) and Gafquat 755N (polyquaternium 11).

The effective particle size can be determined by standard microscopy method as detailed hereinafter in the test methods.

It has also been found that a number of other factors may be selected to beneficially influence the performance of the aminofunctional polysiloxane, such as molecular weight, viscosity, degree of curability, degree of silicone branching (i.e. the number of T and T' groups), the amine type, the linker type and the charge density to molecular weight of nitrogen.

Preferably, the viscosity of the aminofunctional polysiloxane should be selected such that it is in a range of from 10 cps to 3000 cps, preferably from 100 to 500 cps.

Whilst not being bound by theory it is believed that viscosity is proportional to polymer molecular weight and inversely proportional to the degree of branching. Viscosity will impact spreading on hair and ease of processing in the composition. Thus molecular weight also influences both of these important parameters.

The molecular weight of said aminofunctional polysiloxane is preferably from 1000 to 50000, more preferably from 1500 to 35000. The ratio of charge density to molecluar weight of nitrogen is preferably from 190 to 3000.

Whilst not intending to be bound by theory it is believed that increasing the charge density, to a point, provides more affinity for negatively charged, damaged hair, thus improving substantivity and durability through the colour cycle. If charge density is too high, the surfactancy of the silicone is increased to a point where wash-off is achieved too easily and durability thus reduced.

According to the present invention, the hair care composition comprises from 0.1% to 10%, preferably from 0.5% to 5%, most preferably from 1% to 3% by weight of the total composition applied to the hair of the amino functional polysiloxane compound.

It has further been found that the compositions according to the present invention when utilised in conjunction with a hair colouring composition provide, not only the desired initial conditioning as determined by the Combing Technical Test Methods and the Sensory Technical Test Method described hereinafter but also provide conditioning which is also maintained over a number of hair washing cycles.

Accordingly, another aspect of the present invention relates to the provision of a hair colouring composition comprising an aminofunctional polysiloxane according to the formula

$$R_{3-z}Q_zSiO[A]_{x1}[B]_y[C]_sSiQ_zR_{3-z}$$

wherein A is R$_2$SiO, B is RQSiO, C is C=R$_{3-z}$Q$_z$[A]$_{x2}$SiOR' and R is a methyl or hydroxy or methoxy group and at least 50% of said R groups are methyl, R$^1$ is R or Q, Q is an amine functional group of the formula —R$^3$Z, R$^3$ is propyl or isobutyl, Z is NH$_2$ or NHCH$_2$CH$_2$NH$_2$, N$^+$(R$^4$)$_3$A$^-$, —NR$^4$(CH$_2$)$_n$ or N$^+$(R$^4$)$_3$A$^-$, A is F$^-$, Cl$^-$, Br$^-$, I$^-$ and wherein;

t is from 0 to 2, x$_1$ is from 10 to 400, x$_2$ is from 22 to 124, x$_1$+x$_2$ is from 10 to 400, y is from 0 to 9 when z=1, y is from 1 to 9 when z=0;

such that said composition has an initial average Combing Index Value on wet hair of 1 or more, preferably of 1.05, most preferably of 1.08 or more as measured by the Combing Technical Test Method as defined herein, an initial average Sensory Index value of 0.95 or more, preferably of 0.98 or more, most preferably of 1 or more, a final average Combing Index Value on wet hair after 18 washes as measured by the Combing Test Method of 1 or more, preferably of 1.01 or more, most preferably of 1.02 or more and a final average Sensory Index value after 15 washes of 0.95 or more, preferably of 0.98 or, most preferably of 1 or more as defined herein.

According to the present invention the Combing Index value and the Sensory Index value are determined by the test methods described herein after the results of which are applied to the following equations:

Combing Index value =

[{Erase of De-Tangling}Sample]/[{Ease of De-Tangling} Virgin +

[{Ease of Combing} Test]/[Ease of Combing] Virgin]/2

Sensory Index value = [[No Residue] Test/[No Residue] Virgin +

[Not Greasy] Test/[Not Greasy] Virgin +

[Not Coated] Test/[Not Coated] Virgin]/3

Hair Colouring Agents

The composition according to the present application finds particular utility in hair colouring compositions especially oxidative hair colourants wherein the hair is subjected to a particularly aggressive environment.

Oxidative Hair Colouring Agents

A preferred hair colouring agent for use herein is an oxidative hair colouring agent. The concentration of each oxidative hair colouring agent in the colouring compositions according to the present invention is preferably from about 0.0001% to about 5% by weight. The exact amount is dependant upon the end shade required. Typically blond shades comprise from 0.0001% to 1.00%, red shades comprise 0.0010% to 4%, brown shades comprise 0.0100% to 4.00% and black shades comprise 0.100 to 4.00% by weight of the total composition on the hair.

Any oxidative hair colouring agent can be used in the compositions herein. Typically, but without intending to be limited thereby, oxidative hair colouring agents, consist essentially of at least two components, which are collectively referred to as dye forming intermediates (or precursors). Dye forming intermediates can react in the presence of a suitable oxidant to form a coloured molecule.

The dye forming intermediates used in oxidative hair colorants include: aromatic diamines, aminophenols, various heterocycles, phenols, napthols and their various derivatives. These dye forming intermediates can be broadly classified as; primary intermediates and secondary intermediates. Primary intermediates, which are also known as oxidative dye precursors, are chemical compounds which become activated upon oxidation and can then react with each other and/or with couplers to form coloured dye complexes. The secondary intermediates, also known as colour modifiers or couplers, are generally colourless molecules which can form colours in the presence of activated precursors/primary intermediates, and are used with other intermediates to generate specific colour effects or to stabilise the colour.

Primary intermediates suitable for use in the compositions and processes herein include: aromatic diamines, polyhydric phenols, amino phenols and derivatives of these aromatic compounds (e.g., N-substituted derivatives of the amines, and ethers of the phenols). Such primary intermediates are generally colourless molecules prior to oxidation.

While not wishing to be bound by any particular theory it is proposed herein that the process by which colour is generated from these primary intermediates and secondary coupler compounds generally includes a stepwise sequence whereby the primary intermediate can become activated (by oxidation), and then enjoins with a coupler to give a dimeric, conjugated coloured species, which in turn can enjoin with another 'activated' primary intermediate to produce a trimeric conjugated coloured molecule.

Oxidative Dye Precursors

In general terms, oxidative dye primary intermediates include those monomeric materials which, on oxidation, form oligomers or polymers having extended conjugated systems of electrons in their molecular structure. Because of the new electronic structure, the resultant oligomers and polymers exhibit a shift in their electronic spectra to the visible range and appear coloured. For example, oxidative primary intermediates capable of forming coloured polymers include materials such as aniline, which has a single functional group and which, on oxidation, forms a series of conjugated imines and quinoid dimers, trimers, etc. ranging in colour from green to black. Compounds such as p-phenylenediamine, which has two functional groups, are capable of oxidative polymerization to yield higher molecular weight coloured materials having extended conjugated electron systems. Oxidative dyes known in the art can be used in the compositions according to the present invention. A representative list of primary intermediates and secondary couplers suitable for use herein is found in Sagarin, "Cosmetic Science and Technology", "Interscience, Special Ed. Vol. 2 pages 308 to 310. It is to be understood that the primary intermediates detailed below are only by way of example and are not intended to limit the compositions and processes herein.

The typical aromatic diamines, polyhydric phenols, amino phenols, and derivatives thereof, described above as primary intermediates can also have additional substituents on the aromatic ring, e.g. halogen, aldehyde, carboxylic acid, nitro, sulfonic acid and substituted and unsubstituted hydrocarbon groups, as well as additional substituents on the amino nitrogen and on the phenolic oxygen, e.g. substituted and unsubstituted alkyl and aryl groups. Examples of suitable aromatic diamines, amino phenols, polyhydric phenols and derivatives thereof, respectively, are compounds having the general formulas (I), (II) and (III) below:

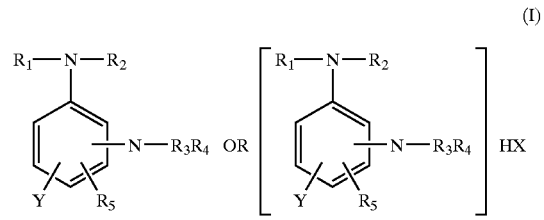

(I)

wherein Y is hydrogen, halogen, (e.g. fluorine, chlorine, bromine or iodine), nitro, amino, hydroxyl,

—COOM or —SO$_3$M (where M is hydrogen or an alkali or alkaline earth metal, ammonium, or substituted ammonium wherein one or more hydrogens on the ammonium ion is replaced with a 1 to 3 carbon atom alkyl or hydroxyalkyl radical), wherein R$_1$, R$_2$, R$_3$ and R$_4$ are the same or different from each other and are selected from the group consisting of hydrogen, C$_1$ to C$_4$ alkyl or alkenyl and C$_6$ to C$_9$ aryl, alkaryl or aralkyl, and R$_5$ is hydrogen, C$_1$ to C$_4$ unsubstituted or substituted alkyl or alkenyl wherein the substituents are selected from those designated as Y, above, or C$_6$ to C$_9$ unsubstituted or substituted aryl, alkaryl or aralkyl wherein the substituents are selected from those defined as Y, above. Since the precursors of formula (I) are amines, they can be used herein in the form of peroxide-compatible salts, as noted, wherein X represents peroxide-compatible anions of the type herein before detailed. The general formula of the salt indicated is to be understood to encompass those salts having mono-, di-, and tri-negative anions.

Specific examples of formula (I) compounds are: o-phenylenediamine, m-phenylenediamine, p-phenylenediamine, 2-chloro-p-phenylenediamine, 2-iodo-p-phenylenediamine, 4-nitro-o-phenylenediamine, 2-nitro-p-phenylenediamine, 1,3,5-triaminobenzene, 2-hydroxy-p-phenylenediamine, 2,4-diaminobenzoic acid, sodium 2,4-diaminobenzoate, calcium di-2,4-diaminobenzoate, ammonium 2,4-diaminobenzoate, trimethylammonium 2,4-, diaminobenzoate, tri-(2-hydroxyethyl)ammonium 2,4-diaminobenzoate, 2,4-diaminobenzaldehyde carbonate, 2,4-diaminobenzensulfonic acid, potassium 2,4-diaminobenzenesulfonate, N,N-diisopropyl-p-, phenylenediamine bicarbonate, N,N-dimethyl-p-phenylenediamine, N-ethyl-N'-(2-propenyl)-p-phenylenediamine, N-phenyl-p-phenylenediamine, N-phenyl-N-benzyl-p-phenylenediamine, N-ethyl-N'-(3-ethylphenyl)-p-phenylenediamine, 2,4-toluenediamine, 2-ethyl-p-phenylenediamine, 2-(2-bromoethyl)-p-phenylenediamine, 2-phenyl-p-phenylenediamine laurate, 4-(2,5-diaminophenyl)benzaldehyde, 2-benzyl-p-phenylenediamine acetate, 2-(4-nitrobenzyl)-p-phenylenediamine, 2-(4-methylphenyl)-p-phenylenediamine, 2-(2,5-diaminophenyl)-5-methylbenzoic acid, methoxyparaphenylenediamine, dimethyl-p-phenylenediamine, 2,5-dimethylpara-phenylenediamine, 2-methyl-5-methoxy-para-phenylenediamine, 2,6-methyl-5-methoxy-para-phenylenediamine, 3-methyl-4-amino-N,N-diethylaniline, N,N-bis(β-hydroxyethyl)-para-phenylenediamine, 3-methyl-4-amino-N,N-bis(β-hydroxyethyl)aniline, 3-chloro-4-amino-N,N-bis(β-hydroxyethyl)aniline, 4-amino-N-ethyl-N-(carbamethyl)aniline, 3-methyl-4-amino-N-ethyl-N-(carbamethyl)aniline, 4-amino-N-ethyl-(β-piperidonoethyl)aniline, 3-methyl-4-amino-N-ethyl-(β-piperidonoethyl)aniline, 4-amino-N-ethyl-N-(β-morpholinoethyl)aniline, 3-methyl-4-amino-N-ethyl-N-(β-morpholinoethyl)aniline, 4-amino-N-ethyl-N-(β-acetylaminoethyl)aniline, 4-amino-N-(β-methoxyethyl)aniline, 3-methyl-4-amino-N-ethyl-N-(β-acetylaminoethyl)aniline, 4-amino-N-ethyl-N-(β-mesylaminoethyl)aniline, 3-methyl-4-amino-N-ethyl-N-(β-mesylaminoethyl)aniline, 4-amino-N-ethyl-N-(β-sulphoethyl)aniline, 3-methyl-4-amino-N-ethyl-N-(β-sulphoethyl)aniline, N-(4-aminophenyl)morpholine, N-(4-aminophenyl)piperidine, 2,3-dimethyl-p-phenylenediamine, isopropyl-p-phenylenediamine, N,N-bis-(2-hydroxyethyl)-p-phenylenediamine sulphate.

Compounds having the general structure (II) are as follows:

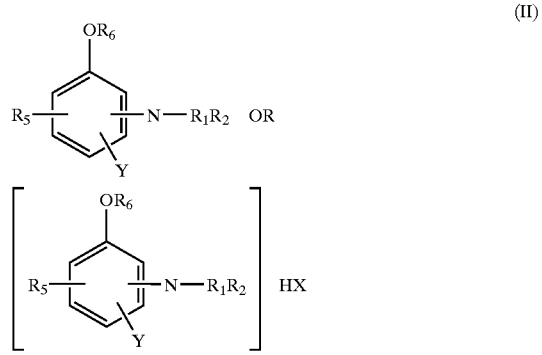

(II)

where X and Y are the same as in formula (I), $R_1$ and $R_2$ can be the same or different from each other and are the same as in formula (I), $R_5$ is the same as in formula (I) and $R_6$ is hydrogen or $C_1$ to $C_4$ substituted or unsubstituted alkyl or alkenyl wherein the substituents are selected from those defined as Y in formula (I).

Specific examples of formula (II) compounds are: o-aminophenol, m-aminophenol, p-aminophenol, 2-iodo-p-aminophenol, 2-nitro-p-aminophenol, 3,4-dihydroxyaniline, 3,4-diaminophenol, chloroacetate, 2-hydroxy-4-aminobenzoic acid, 2-hydroxy-4-aminobenzaldehyde, 3-amino-4-hydroxybenzenesulfonic acid, N,N-diisopropyl-p-aminophenol, N-methyl-N-(1-propenyl)-p-aminophenol, N-phenyl-N-benzyl-p-aminophenol sulphate, N-methyl-N-(3-ethylphenyl)-p-aminophenol, 2-nitro-5-ethyl-p-aminophenol, 2-nitro-5-(2-bromoethyl)-p-aminophenol, (2-hydroxy-5-aminophenyl)acetaldehyde, 2-methyl-p-aminophenol, (2-hydroxy-5-aminophenyl)acetic acid, 3-(2-hydroxy-5-aminophenyl)-1-propene, 3-(2-hydroxy-5-aminophenyl)-2-chloro-1-propene, 2-phenyl-p-aminophenol palmitate, 2-(4-nitrophenyl)-p-aminophenol, 2-benzyl-p-aminophenol, 2-(4-chlorobenzyl-p-aminophenol perchlorate, 2-(4-methylphenyl)-p-aminophenol, 2-(2-amino-4-methylphenyl)-p-aminophenol, p-methoxyaniline, 2-bromoethyl-4-aminophenyl ether phosphate, 2-nitroethyl-4-aminophenyl ether bromide, 2-aminoethyl-4-aminophenyl ether, 2-hydroxyethyl-4-aminophenyl ether, (4-aminophenoxy)acetaldehyde, (4-aminophenoxy)acetic acid, (4-aminophenoxy)methanesulfonic acid, 1-propenyl-4-aminophenyl ether isobutyrate, (2-chloro)-1-propenyl-4-aminophenyl ether, (2-nitro)-1-propenyl-4-aminophenyl ether, (2-amino)-propenyl-4-aminophenyl ether, (2-hydroxy)-1-propenyl-4-aminophenyl ether, N-methyl-p-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2,5-dimethyl-4-aminophenol, 2-hydroxymethyl-4-aminophenol, 3-hydroxymethyl-4-aminophenol, 2,6-dichloro-4-aminophenol, 2,6-dibromo-4-aminophenol and 2-bromo-4-aminophenol.

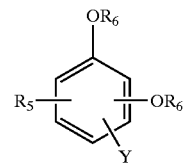

(III)

Specific examples of formula (III) compounds are: o-hydroxyphenol (catechol), m-hydroxyphenol (resorcinol), p-hydroxyphenol (hydroquinone), 4-methoxyphenol, 2-methoxyphenol, 4-(2-chloroethoxy) phenol, 4-(2-propenoxy) phenol, 4-(3-chloro-2-propenoxy)phenol, 2-chloro-4-hydroxyphenol (2-chlorohydroqinone), 2-nitro-4-hydroxyphenol(2-nitrohydroquinone), 2-amino-4-hydroxyphenol, 1,2,3-trihydroxybenzene (pyrogallol), 2,4-dihydroxybenzaldehyde, 3,4-dihydoxybenzoic acid, 2,4-dihydroxybenzenesulfonic acid, 3-ethyl-4-hydroxyphenol, 3-(2-nitroethyl)-4-hydroxyphenol, 3-(2-propenyl)-4-hydroxyphenol, 3-(3-chloro-2-propenyl)-4-hydroxyphenol, 2-phenyl-4-hydroxyphenol, 2-(4-chlorophenyl)-4-hydroxyphenol, 2-benzyl-4-hydroxyphenol, 2-(2-nitrophenyl)-4-hydroxyphenol, 2-(2-methylphenyl)-4-hydroxyphenol, 2-(2-methyl-4-chlorophenyl)-4-hydroxyphenol, 3-methoxy-4-hydroxy-benzaldehyde, 2-methoxy-4-(1-propenyl)phenol, 4-hydroxy-3-methoxycinnamic acid, 2,5-dimethoxyaniline, 2-methylresorcinol, alpha napthol and salts thereof. Secondary coupling compounds which are suitable for inclusion in the colouring compositions and processes herein before described include certain aromatic amines and phenols and derivatives thereof which do not produce colour singly, but which modify the colour, shade or intensity of the colours developed by the primary oxidised dye intermediates. Certain aromatic amines and phenolic compounds, and derivatives thereof, including some aromatic diamines and polyhydric phenols of the types described by formulas (I), (Ia), (Ib), (II) and (III) above, but which are well known in the art not to be suitable primary intermediates, are suitable as couplers herein. Polyhydric alcohols are also suitable for use as couplers herein.

The aromatic amines and phenols and derivatives described above as couplers can also have additional substituents on the aromatic ring, e.g., halogen, aldehyde, carboxylic acid, nitro, sulfonyl and substituted and unsubstituted by hydrocarbon groups, as well as additional substituents on the amino nitrogen, or phenolic oxygen, e.g. substituted and unsubstituted alkyl and aryl groups. Again, peroxide-compatible salts thereof are suitable for use herein.

Examples of aromatic amines, phenols and derivatives thereof are compounds of the general formulas (IV) and (V) below:

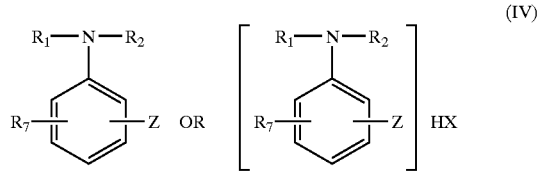

(IV)

wherein Z is hydrogen, $C_1$ and $C_3$ alkyl, halogen (e.g. fluorine, chlorine, bromine or iodine) nitro,

—COOM or $SO_3M$, (where M is hydrogen or an alkali or alkaline earth metal, ammonium or substituted ammonium wherein one or more hydrogen atoms on the ammonium ion is replaced with 1 to 3 carbon atom alkyl or hydroxyalkyl radical), wherein $R_1$ and $R_2$ are the same or different and are selected from the group consisting of hydrogen, $C_1$ to $C_4$ alkyl or alkenyl and $C_6$ to $C_9$ aryl, alkaryl or aralkyl and $R_7$ is hydrogen, $C_1$ to $C_4$ unsubstituted or substituted alkyl or alkenyl wherein the substituents are selected from those designated as Z above or $C_6$ to $C_9$ unsubstituted or substituted aryl, alkaryl or aralkyl wherein the substituents are selected from those defined as Z above and wherein X is as defined in formula (I).

Specific examples of formula (IV) compounds are: aniline, p-chloroaniline, p-fluoroaniline, p-nitroaniline, p-aminobenzaldehyde, p-aminobenzoic acid, sodium-p-aminobenzoate, lithium-p-aminobenzoate, calcium di-p-aminobenzoate, ammonium-p-aminobenzoate, trimethylammonium-p-aminobenzoate, tri(2-hydroxyethyl)-p-aminobenzoate, p-aminobenzenesulfonic acid, potassium p-aminobenzenesulfonate, N-methylaniline, N-propyl-N-phenylaniline, N-methyl-N-2-propenylaniline, N-benzylaniline, N-(2-ethylphenyl)aniline, 4-methylaniline, 4-(2-bromoethyl)aniline, 2-(2-nitroethyl)aniline, (4-aminophenyl)acetaldehyde, (4-aminophenyl)acetic acid, 4-(2-propenyl)aniline acetate, 4-(3-bromo-2-propenyl) aniline, 4-phenylaniline chloroacetate, 4-(3-chlorophenyl) aniline, 4-benzylaniline, 4-(4-iodobenzyl)aniline, 4-(3-ethylphenyl)aniline, 4-(2-chloro-4-ethylphenyl)aniline.

(V)

wherein Z and $R_7$ are defined as in formula (IV) and $R_8$ is hydrogen or $C_1$ to $C_4$ substituted or unsubstituted alkyl or alkenyl wherein the substituents are selected from those defined as Z in formula (IV).

Specific examples of formula (V) compounds are: phenol, p-chlorophenol, p-nitrophenol, p-hydroxybenzaldehyde, p-hydroxybenzoic acid, p-hydroxybenzenesulfonic acid, ethylphenyl ether, 2-chloroethylphenyl ether, 2-nitroethylphenyl ether, phenoxyacetaldehyde, phenoxyacetic acid, 3-phenoxy-1-propene, 3-phenoxy-2-nitro-1-propene, 3-phenoxy-2-bromo-1-propene, 4-propylphenol, 4-(3-bromopropyl) phenol, 2-(2-nitroethyl)phenol, (4-hydroxyphenyl) acetaldehyde, (4-hydroxyphenyl)acetic acid, 4-(2-propenyl) phenol, 4-phenylphenol, 4-benzylphenol, 4-(3-fluoro-2-propenyl)phenol, 4-(4-chlorobenzyl)phenol, 4-(3-ethylphenyl)phenol, 4-(2-chloro-3-ethylphenyl)phenol, 2,5-xylenol, 2,5-diaminopyridine, 2-hydroxy-5-aminopyridine, 2-amino-3-hydroxy pyridine, tetraaminopyrimindine, 1,2,4-trihydroxybenzene, 1,2,4-trihydroxy-5-($C_1$–$C_6$-alkyl) benzene, 1,2,3-trihydroxybenzene, 4-aminoresorcinol, 1,2-dihydroxybenzene, 2-amino-1,4-dihydroxybenzene, 2-amino-4-methoxy-phenol, 2,4-diaminophenol, 3-methoxy-1,2-dihydroxybenzene, 1,4-dihydroxy-2-(N,N-diethylamino)-benzene, 2,5-diamino-4-methoxy-1-hydroxybenzene, 4,6-dimethoxy-3-amino-1-hydroxybenzene, 2,6-dimethyl-4-[N-(p-hydroxyphenyl) amino]-1-hydroxybenzene, 1,5-diamino-2-methyl-4-[N-(p-hydroxyphenyl)amino]benzene and salts thereof.

Additional primary intermediates suitable for use herein include catechol species and in particular catechol "dopa" species which includes dopa itself as well as homologs, analogs and derivatives of DOPA. Examples of suitable cachetol species include cysteinyl dopa, alpha alkyl dopa having 1 to 4, preferably 1 to 2 carbon atoms in the alkyl group, epinephrine and dopa alkyl esters having 1 to 6, preferably 1 to 2 carbon atoms in the alkyl group.

In general suitable catechols are represented by formula (VI) below:

(VI)

wherein $R_1$, $R_2$ and $R_3$, which may be the same or different, are electron donor or acceptor substituents selected from H, lower ($C_1$–$C_6$) alkyl, OH, OR, COOR, NHCOR, CN, COOH, Halogen, $NO_2$, $CF_3$, $SO_3H$ or $NR_4R_5$, with the proviso that only one of the $R_1$, $R_2$ or $R_3$ can be CN, COOH, halogen, $NO_2$, $CF_3$ or $SO_3H$: $R_4$ and $R_5$, which may be the same or different, are H, lower ($C_1$–$C_6$) alkyl or substituted lower ($C_1$–$C_6$) alkyl in which the substituent may be OH, OR, $NHCOR_6$, $NHCONH_2$, $NHCO_2R_6$, $NHCSNH_2$, CN, COOH, $SO_3H$, $SO_2NR_6$, $SO_2R_6$ or $CO_2R_6$; $R_6$ is lower ($C_1$–$C_6$) alkyl, lower ($C_1$–$C_6$) hydroxyalkyl phenyl linked to the nitrogen by an alkylene chain, phenyl or substituted phenyl with the substituent defined as $R_1$, and R is $C_1$–$C_6$ alkyl or $C_1$–$C_6$ hydroxyalkyl.

Also included herein are oxidative hair colouring agents of the formula:

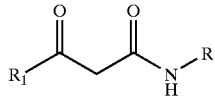

wherein: $R_1$=substituted or unsubstituted benzene ring, tertiary-butyl, etc.; R=substituted or unsubstituted benzene ring and the formula:

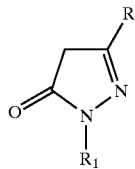

wherein R=aminoalkyl, amidoalkyl, aminobenzene (substituted or unsubstituted), amidobenzene (substituted or unsubstituted), alkyl, substituted or unsubstituted benzene ring; $R_1$=substituted or unsubstituted benzene ring.

The primary intermediates can be used herein alone or in combination with other primary intermediates, and one or more can be used in combination with one or more couplers. The choice of primary intermediates and couplers will be determined by the colour, shade and intensity of coloration which is desired. There are nineteen preferred primary intermediates and couplers which can be used herein, singly or in combination, to provide dyes having a variety of shades ranging from ash blonde to black; these are: pyrogallol, resorcinol, p-toluenediamine, p-phenylenediamine, o-phenylenediamine, m-phenylenediamine, o-aminophenol, p-aminophenol, 4-amino-2-nitrophenol, nitro-p-phenylenediamine, N-phenyl-p-phenylenediamine, m-aminophenol, 2-amino-3-hydroxypyridine, 1-napthol, N,Nbis(2-hydroxyethyl)p-phenylenediamine, 4-amino-2-hydroxytoluene, 1,5-dihydroxynapthalene, 2-methyl resorcinol and 2,4-diaminoanisole. These can be used in the molecular form or in the form of peroxide-compatible salts, as detailed above.

For example low intensity colours such as natural blond to light brown hair shades generally comprise from about 0.001% to about 5%, preferably from about 0.1% to about 2%, more preferably from about 0.2% to about 1% by weight of colouring composition of total oxidative dyeing agents and may be achieved by the combination of primary intermediates such as 1,4-diamino-benzene, 2,5-diamino toluene, 2,5-diamino-anisole, 4-aminophenol, 2,5-diamino-benzyl alcohol and 2-(2',5'-diamino)phenyl-ethanol with couplers such as resorcinol, 2-methyl resorcinol or 4-chloro resorcinol.

Similarly combination of the above primary intermediates with couplers, such as, 5-amino-2-methyl phenol and 1,3-diamino-benzene derivatives such as 2,4-diamino-anisole at levels of from about 0.5% to about 1% of total dyeing agents can lead to medium intensity red colours. High intensity colours such as blue to blue-violet hair shades can be produced by the combination of the above primary intermediates with couplers such as 1,3-diamino-benzene or its derivatives such as 2,5-diamino-toluene at levels of from about 1% to about 6% by weight of composition of total dyeing agents. Black hair colours can be obtained by combining the aforementioned primary intermediates with couplers such as 1,3-diaminobenzene or its derivatives.

Non-oxidative and Other Hair Colouring Agents

The hair colouring compositions of the present invention may, in addition to or instead of an oxidative hair colouring agent, include non-oxidative and other dye materials. Optional non-oxidative and other dyes suitable for use in the hair colouring compositions and processes according to the present invention include both semi-permanent, temporary and other dyes. Non-oxidative dyes as defined herein include the so-called 'direct action dyes', metallic dyes, metal chelate dyes, fibre reactive dyes and other synthetic and natural dyes. Various types of non-oxidative dyes are detailed in: 'Chemical and Physical Behaviour of Human Hair' 3rd Ed. by Clarence Robbins (pp250–259); 'The Chemistry and Manufacture of Cosmetics'. Volume IV. 2nd Ed. Maison G. De Navarre at chapter 45 by G. S. Kass (pp841–920); 'cosmetics: Science and Technology' 2nd Ed., Vol. II Balsam Sagarin, Chapter 23 by F. E. Wall (pp 279–343); 'The Science of Hair Care' edited by C. Zviak, Chapter 7 (pp 235–261) and 'Hair Dyes', J. C. Johnson, Noyes Data Corp., Park Ridge, U.S.A. (1973), (pp 3–91 and 113–139).

Direct action dyes which do not require an oxidative effect in order to develop the colour, are also designated hair tints and have long been known in the art. They are usually applied to the hair in a base matrix which includes surfactant material. Direct action dyes include nitro dyes such as the derivatives of nitroamino benzene or nitroaminophenol; disperse dyes such as nitroaryl amines, aminoanthraquinones or azo dyes; anthraquinone dyes, naphthoquinone dyes; basic dyes such as Acridine Orange C.I. 46005. In the case of direct dyes, these are preferably used in combination with an oxidative hair colouring agent in the compositions herein.

Nitrodyes are added to dyeing compositions to enhance colour of colorant and to add suitable aesthetic colour to the dye mixture prior to application. Further examples of direct action dyes include the Arianor dyes basic brown 17, C.I. (colour index)—no. 12,251; basic red 76, C.I.—12,245; basic brown 16, C.I.—12,250; basic yellow 57, C.I.—12, 719 and basic blue 99, C.I.—56,059 and further direct action dyes such as acid yellow 1, C.I.—10,316 (D&C yellow no.7); acid yellow 9, C.I.—13,015; basic violet C.I.—45, 170; disperse yellow 3, C.I.—11,855; basic yellow 57, C.I.—12,719; disperse yellow 1, C.I.—10,345; basic violet 1, C.I.—42,535, basic violet 3, C.I.—42,555; greenish blue, C.I.—42090 (FD&C Blue no.1); yellowish red, C.I.—14700 (FD&C red no.4); yellow, C.I.19140 (FD&C yellow no5); yellowish orange, C.I.15985 (FD&C yellow no.6); bluish green, C.I.42053 (FD&C green no.3); yellowish red, C.I.16035 (FD&C red no.40); bluish green, C.I.61570 (D&C green no.3); orange, C.I.45370 (D&C orange no.5); red, C.I.15850 (D&C red no.6); bluish red, C.I.15850 (D&C red no.7); slight bluish red, C.I.45380 (D&C red no.22); bluish red, C.I.45410 (D&C red no.28); bluish red, C.I.73360 (D&C red no.30); reddish purple, C.I.17200 (D&C red no.33); dirty blue red, C.I.15880 (D&C red no.34); bright yellow red, C.I.12085 (D&C red no.36); bright orange, C.I.15510 (D&C orange no.4); greenish yellow, C.I.47005 (D&C yellow no.10); bluish green, C.I.59040 (D&C green no.8); bluish violet, C.I.60730 (Ext. D&C violet no.2); greenish yellow, C.I.10316 (Ext. D&C yellow no.7).

Fibre reactive dyes include the Procion (RTM), Drimarene (RTM), Cibacron (RTM), Levafix (RTM) and Remazol (RTM) dyes available from ICI, Sandoz, Ciba-Geigy, Bayer and Hoechst respectively.

Natural dyes and vegetable dyes as defined herein include henna (*Lawsonia alba*), camomile (*Matricaria chamomila* or *Anthemis nobilis*), indigo, logwood and walnut hull extract.

Temporary hair dyes, or hair colouring rinses, are generally comprised of dye molecules which are too large to diffuse into the hair shaft and which act on the exterior of the hair. They are usually applied via a leave-in procedure in which the dye solution is allowed to dry on the hair surface. As such these dyes are typically less resistant to the effects of washing and cleaning the hair with surface active agents and are washed off of the hair with relative ease. Any temporary hair dye may suitably be used in the compositions of the invention and examples of preferred temporary hair dyes are illustrated below. Temporary dyes are preferably used together with an oxidative colouring agent in the composition herein.

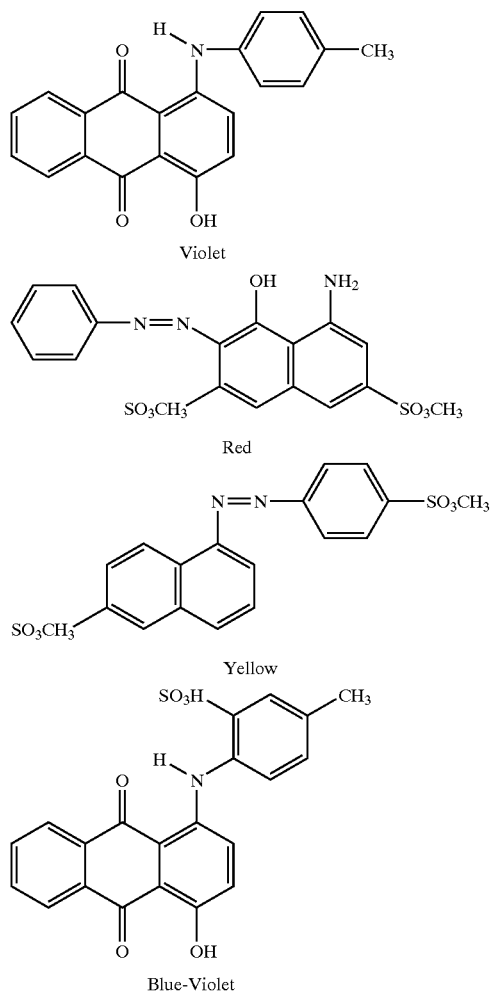

Semi-permanent hair dyes are dyes which are generally smaller in size and effect to temporary hair rinses but are generally larger than permanent (oxidative) dyes. Typically, semi-permanent dyes act in a similar manner to oxidative dyes in that they have the potential to diffuse into the hair shaft. However, semi-permanent dyes are generally smaller in size than the aforementioned conjugated oxidative dye molecules and as such are pre-disposed to gradual diffusion out of the hair again. Simple hair washing and cleaning action will encourage this process and in general semi-permanent dyes are largely washed out of the hair after about 5 to 8 washes. Any semi-permanent dye system may be suitably used in the compositions of the present invention. Suitable semi-permanent dyes for use in the compositions of the present invention are HC Blue 2, HC Yellow 4, HC Red 3, Disperse Violet 4, Disperse Black 9, HC Blue 7, HC Yellow 2, Disperse Blue 3, Disperse violet 1 and mixtures thereof. Examples of semi-permanent dyes are illustrated below:

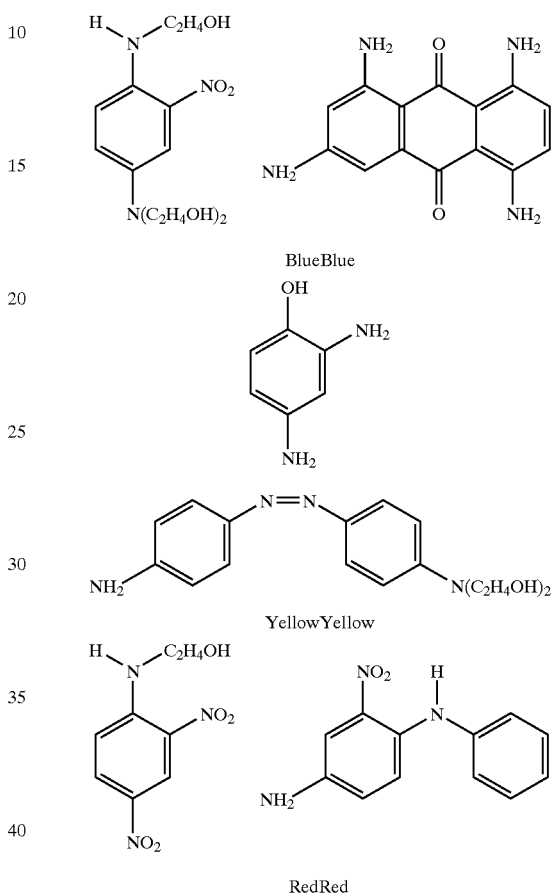

Typical semi-permanent dye systems incorporate mixtures of both large and small colour molecules. As the size of the hair is not uniform from root to tip the small molecules will diffuse both at the root and tip, but will not be retained within the tip, while the larger molecules will be generally only be able to diffuse into the ends of the hair. This combination of dye molecule size is used to help give consistent colour results from the root to the tip of the hair both during the initial dyeing process and during subsequent washing.

Oxidising Agents

The hair colouring compositions herein preferably comprise at least one oxidising agent, which may be an inorganic or organic oxidising agent. The oxidising agent is preferably present in the colouring composition at a level of from about 0.01% to about 10%, preferably from about 0.01% to about 6%, more preferably from about 1% to about 4% by weight of the composition.

Inorganic Oxidising Agents

A preferred oxidising agent for use herein is an inorganic peroxygen oxidising agent. The inorganic peroxygen oxidising agent should be safe and effective for use in the compositions herein. Preferably, the inorganic peroxygen oxidising agents suitable for use herein will be soluble in the compositions according to the present invention when in liquid form or in the form intended to be used. Preferably, inorganic peroxygen oxidising agents suitable for use herein will be water-soluble. Water soluble oxidising agents as defined herein means agents which have a solubility to the extent of about 10 g in 1000 ml of deionised water at 25° C. ("Chemistry" C. E. Mortimer. 5th Edn. p277).

The inorganic peroxygen oxidising agents useful herein are generally inorganic peroxygen materials capable of yielding peroxide in an aqueous solution. Inorganic peroxygen oxidising agents are well known in the art and include hydrogen peroxide, inorganic alkali metal peroxides such as sodium periodate, sodium perbromate and sodium peroxide, and inorganic perhydrate salt oxidising compounds, such as the alkali metal salts of perborates, percarbonates, perphosphates, persilicates, persulphates and the like. These inorganic perhydrate salts may be incorporated as monohydrates, tetrahydrates etc. Mixtures of two or more of such inorganic peroxygen oxidising agents can be used if desired. While alkali metal bromates and iodates are suitable for use herein the bromates are preferred. Highly preferred for use in the compositions according to the present invention is hydrogen peroxide.

In preferred colouring compositions herein the inorganic peroxygen oxidising agent is present at a level of from about 0.01% to less than about 6%, preferably from about 0.01% to about 4%, more preferably from about 1% to about 4%, more preferably from about 2% to about 3% by weight of the total composition on hair.

Preformed Organic Peroxyacid

The compositions herein may instead or in addition to the inorganic peroxygen oxidising agent(s), comprise one or more preformed organic peroxyacid oxidising agents.

Suitable organic peroxyacid oxidising agents for use in the colouring compositions according to the present invention have the general formula:

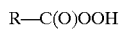

wherein R is selected from saturated or unsaturated, substituted or unsubstituted, straight or branched chain, alkyl, aryl or alkaryl groups with from 1 to 14 carbon atoms.

A class of organic peroxyacid compounds suitable for use herein are the amide substituted compounds of the following general formulae:

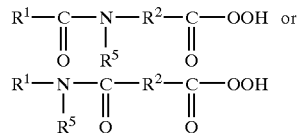

wherein $R^1$ is, a saturated or unsaturated alkyl or alkaryl group, or an aryl group, having from 1 to 14 carbon atoms, $R^2$ is, a saturated or unsaturated alkyl or alkaryl group, or an aryl group, having from 1 to 14 carbon atoms, and $R^5$ is H or, a saturated or unsaturated alkyl or alkaryl group, or an aryl group, having from 1 to 10 carbon atoms. Amide substituted organic peroxyacid compounds of this type are described in EP-A-0,170,386.

Other suitable organic peroxyacid oxidising agents include peracetic, pernanoic, nonylamidoperoxycaproic acid (NAPCA), perbenzoic, m-chloroperbenzoic, di-peroxyisophthalic, mono-peroxyphthalic, peroxylauric, hexanesulphonyl peroxy propionic, N,N-phthaloylamino peroxycaproic, monoper succinic, nonanoyloxybenzoic, dodecanedioyl-monoperoxybenzoic, nonylamide of peroxyadipic acid, diacyl and tetraacylperoxides, especially diperoxydodecanedioic acid, diperoxytetradecanedioic acid and diperoxyhexadecanedioic acid and derivatives thereof. Mono- and diperazelaic acid, mono- and diperbrassylic acid and N-phthaloylaminoperoxicaproic acid and derivatives thereof are also suitable for use herein.

The preformed organic peroxyacid oxidising agents should be safe and effective for use in the compositions herein. Preferably, the preformed organic peroxyacid oxidising agents suitable for use herein will be soluble in the compositions used according to the present invention when in liquid form and in the form intended to be used. Preferably, organic peroxyacid oxidising agents suitable for use herein will be water-soluble. Water-soluble preformed organic peroxyacid oxidising agents as defined herein means agents which have a solubility to the extent of about 10 g in 1000 ml of deionised water at 25° C. ("Chemistry" C. E. Mortimer. 5th Edn. p277).

The preferred peroxyacid materials suitable for use herein are selected from peracetic and pernanoic acids and mixtures thereof.

The preformed organic peroxyacid oxidising agent, where present, is preferably present at a level of from about 0.01% to about 8%, more preferably from about 0.1% to about 6%, most preferably from about 0.2% to about 4%, and especially from about 0.3% to about 3% by weight of the hair colouring composition.

When both an inorganic peroxygen oxidising agent and a preformed organic peroxy acid are present in the compositions herein, the weight ratio of the inorganic peroxygen oxidising agent to the preformed organic peroxy acid is preferably in the range of from about 0.0125:1 to about 500:1, more preferably from about 0.0125:1 to about 50:1. In addition to the inorganic peroxygen oxidising agents and the preformed organic peroxyacid oxidising agents suitable for use herein, the compositions according to the present invention may optionally comprise additional organic peroxides such as urea peroxide, melamine peroxide and mixtures thereof. The level of organic peroxide, where present, is from about 0.01% to about 3%, preferably from about 0.01% to about 2%, more preferably from about 0.1% to about 1.5% and most preferably from about 0.2% to about 1% by weight of composition.

Conditioning Agent

The hair care composition according to the present invention preferably comprises at least one hair conditioning agent in addition to the aminofunctional polysiloxane. The conditioning agent herein can be any conditioning agent suitable for use in conditioning hair. The incorporation of an additional conditioning agent can further improve the condition of the hair.

The conditioning agent is preferably present at a level of from about 0.1% to about 25%, preferably from about 1% to about 20%, more preferably from about 5% to about 20% and especially from about 5% to about 15%, by weight of the composition.

Suitable conditioning agents for use herein include, but are not limited to, cationic surfactants, cationic polymers, insoluble silicones, non-volatile hydrocarbons, saturated C14–C22 straight chain fatty alcohols, non-volatile hydrocarbon esters, and mixtures thereof. Other suitable conditioning agents are disclosed in WO95/20939 and WO96/32919 which are incorporated herein by reference.

Preferred conditioning agents for use herein include cationic surfactants, cationic polymers, insoluble silicone conditioning agents and saturated C14–C22 straight chain fatty alcohols and mixtures thereof. Especially preferred for use herein is a mixture of cationic polymer, non-volatile silicone and C14–C22 straight chain fatty alcohols.

When present, the insoluble silicone conditioning agents are present at a level of from about 0.1 to 10%, preferably from about 0.1% to about 5%, more preferably from about 1% to about 3% by weight of composition. Suitable insoluble silicones include polyalkyl siloxanes, polyaryl siloxanes, polyalkylaryl siloxanes, polether siloxane copolymers, and mixtures thereof. The silicone conditioning agent will preferably be non-volatile. As used herein the term "non-volatile" shall mean that the material has a boiling point of at least about 260° C., preferably at least about 275° C., more preferably at least about 300° C. Such materials exhibit very low or no significant vapour pressure at ambient conditions. The term "silicone fluid" shall mean flowable silicone materials having a viscosity of less than 1,000,000 centistokes at 25° C. The term "silicone gum" shall mean flowable silicone materials having a viscosity of 1,000,000 centistokes at 25° C. or greater. The viscosity can be measured by a glass capillary viscometer as in Dow Corning Corporate Test Method CTM0004, Jul. 20, 1920, or equivalent.

A preferred silicone material for use herein is a polydimethyl siloxane. These silicones are available for example from the General Electric Company in their Viscasil and SF96 series, and from Dow Corning in their Dow Corning 200 series.

Other suitable insoluble silicones for use herein are disclosed in WO96/32919 which is incorporated herein by reference.

When present, the cationic polymers are present at a level of from about 0.1 to 10%, preferably from about 0.1% to about 5%, more preferably from about 1% to about 3% by weight of composition. Suitable cationic polymers for use herein are disclosed in WO96/32919 which is incorporated herein by reference.

When present, the fatty alcohols are present at a level of from about from about 0.1% to about 20%, preferably from about 1% to about 15% and more preferably from about 3% to about 10% by weight of composition. Preferred fatty alcohols for use herein are cetyl alcohol and stearyl alcohol and mixtures thereof.

The colouring compositions used in the methods of the present invention can be formulated over a wide pH range, e.g. from about 2 to about 13, but the compositions are formulated at high pH, preferably in a pH range of from about 8 to about 12, more preferably from about 9 to about 11, most preferably from about 9.5 to 10.5.

The compositions may contain one or more optional buffering agents and/or hair swelling agents (HSAs). Several different pH modifiers can be used to adjust the pH of the final composition or any constituent part thereof. However, preferred compositions herein are substantially free of additional buffering agents, buffering agents and hair swelling agents, i.e. they comprise less than about 1%, preferably less than about 0.5%, more preferably less than about 0.1% by weight of such agents.

This pH adjustment can be effected by using well known acidifying agents in the field of treating keratinous fibres, and in particular human hair, such as inorganic and organic acids such as hydrochloric acid, tartaric acid, citric acid, succinic acid, phosphoric acid and carboxylic or sulphonic acids such as ascorbic acid, acetic acid, lactic acid, sulphuric acid, formic acid, ammonium sulphate and sodium dihydrogenphosphate/phosphoric acid, disodium hydrogenphosphate/phosphoric acid, potassium chloride/hydrochloric acid, potassium dihydrogen phthalate/hydrochloric acid, sodium citrate/hydrochloric acid, potassium dihydrogen citrate/hydrochloric acid, potassium dihydrogencitrate/citric acid, sodium citrate/citric acid, sodium tartarate/tartaric acid, sodium lactate/lactic acid, sodium acetate/acetic acid, disodium hydrogenphosphate/citric acid and sodium chloride/glycine/hydrochloric acid, succinic acid and mixtures thereof.

Examples of alkaline buffering agents are ammonium hydroxide, ethylamine, dipropylamine, triethylamine and alkanediamines such as 1,3-diaminopropane, anhydrous alkaline alkanolamines such as, mono or di-ethanolamine, preferably those which are completely substituted on the amine group such as dimethylaminoethanol, polyalkylene polyamines such as diethylenetriamine or a heterocyclic amine such as morpholine as well as the hydroxides of alkali metals, such as sodium and potassium hydroxide, hydroxides of alkali earth metals, such as magnesium and calcium hydroxide, basic amino acids such as L-argenine, lysine, alanine, leucine, iso-leucine, oxylysine and histidine and alkanolamines such as dimethylaminoethanol and aminoalkylpropanediol and mixtures thereof. Also suitable for use herein are compounds other than ammonium carbonate or ammonium carbamate that form $HCO_3^-$ by dissociation in water (hereinafter referred to as 'ion forming compounds'). Examples of suitable ion forming compounds are $Na_2CO_3$, $NaHCO_3$, $K_2CO_3$, $NH_4HCO_3$, $CaCO_3$ and $Ca(HCO_3)$ and mixtures thereof.

The hair colour compositions herein, may, as will be described later herein, comprise a final composition containing a hair colouring agent and a conditioning agent which have been admixed prior to application to the hair or may comprise a single component system. As such, the compositions herein may comprise colouring kits of a number of separate components.

In oxidative colouring kits comprising a portion of inorganic peroxygen oxidising agent, such as hydrogen peroxide, which may be present in either solid or liquid form, a buffering agent solution can be used to stabilise hydrogen peroxide. Since hydrogen peroxide is stable in the pH range from 2 to 4, it is preferable to use a buffering agent having a pH within this range. Dilute acids are suitable hydrogen peroxide buffering agents.

Catalyst

The compositions herein may optionally contain a transition metal containing catalyst for the inorganic peroxygen oxidising agents and the, optional, preformed peroxy acid oxidising agent(s). Suitable catalysts for use herein are disclosed in WO98/27945 which is incorporated herein by reference.

Heavy Metal Ion Sequestrant

The compositions herein may contain as an optional component a heavy metal ion sequestrant. By heavy metal ion sequestrant it is meant herein components which act to sequester (chelate or scavenge) heavy metal ions. These components may also have calcium and magnesium chelation capacity, but preferentially they show selectivity to binding heavy metal ions such as iron, manganese and copper. Such sequestering agents are valuable in hair colouring compositions as herein described for the delivery of controlled oxidising action as well as for the provision of good storage stability of the hair colouring products.

Heavy metal ion sequestrants are generally present at a level of from about 0.005% to about 20%, preferably from about 0.01% to about 10%, more preferably from about 0.05% to about 2% by weight of the compositions. Suitable sequestering agents are disclosed in WO98/27945 which is incorporated herein by reference in its entirety.

Thickeners

The compositions of the present invention may additionally include a thickener at a level of from about 0.05% to about 20%, preferably from about 0.1% to about 10%, more preferably from about 0.5% to about 5% by weight. Thickening agents suitable for use in the compositions herein are selected from oleic acid, cetyl alcohol, oleyl alcohol, sodium chloride, cetearyl alcohol, stearyl alcohol, synthetic thickeners such as Carbopol, Aculyn and Acrosyl and mixtures thereof. Preferred thickeners for use herein are Aculyn 22 (RTM), steareth-20 methacrylate copolymer; Aculyn 44 (RTM), polyurethane resin and Acusol 830 (RTM), acrylates copolymer which are available from Rohm and Haas, Philadelphia, Pa., USA. Additional thickening agents suitable for use herein include sodium alginate or gum arabic, or cellulose derivatives, such as methyl cellulose or the sodium salt of carboxymethylcellulose or acrylic polymers.

Diluent

Water is the preferred diluent for the compositions according to the present invention. However, the compositions according to the present invention may include one or more solvents as additional diluent materials. Generally, solvents suitable for use in the colouring compositions of the present invention are selected to be miscible with water and innocuous to the skin. Solvents suitable for use as additional diluents herein include $C_1$–$C_{20}$ mono- or polyhydric alcohols and their ethers, glycerine, with monohydric and dihydric alcohols and their ethers preferred. In these compounds, alcoholic residues containing 2 to 10 carbon atoms are preferred. Thus, a preferred group includes ethanol, isopropanol, n-propanol, butanol, propylene glycol, ethylene glycol monoethyl ether, and mixtures thereof. Water is the preferred principal diluent in the compositions according to the present invention. Principal diluent, as defined herein, means, that the level of water present is higher than the total level of any other diluents.

The diluent is present at a level preferably of from about 5% to about 99.98%, preferably from about 15% to about 99.5%, more preferably at least from about 30% to about 99%, and especially from about 50% to about 98% by weight of the compositions herein.

Enzyme

A further additional material useful in the hair colouring compositions herein is one or more enzymes. Suitable enzymatic materials include the commercially available lipases, cutinases, amylases, neutral and alkaline proteases, esterases, cellulases, pectinases, lactases and peroxidases conventionally incorporated into detergent compositions. Suitable enzymes are discussed in U.S. Pat. Nos. 3,519,570 and 3,533,139 and in WO98/27945 which is incorporated herein by reference in its entirety.

Surfactant Materials

The compositions herein can additionally contain a surfactant system. Suitable surfactants for inclusion in the compositions for use in the invention generally have a lipophilic chain length of from about 8 to about 22 carbon atoms and can be selected from anionic, cationic, nonionic, amphoteric, zwitterionic surfactants and mixtures thereof. Particularly preferred are cationic, nonionic and mixtures thereof. Suitable surfactants for use herein are disclosed in WO98/27945 which is incorporated herein by reference in its entirety. Particularly preferred surfactants are surfactants of the general formula

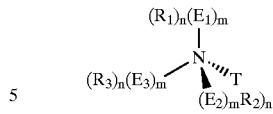

Wherein $R_1$, $R_2$, and $R_3$ represent either hydrogen or organic radicals with n equal to 0 or an integer. The radicals may be saturated, unsaturated or aromatic in nature with carbon chain lengths of 1 to 24. $R_1$, $R_2$ and $R_3$ may contain heteroatoms such as, but not limited to, oxygen, nitrogen and sulphur. $E_1$, $E_2$ and $E_3$ represent polyethyleneoxide moieties with ethyleneoxide sub-units such that m can be zero or an integer. The degree of ethoxylation of $E_1$, $E_2$ and $E_3$ can be the same or different. T represents a hydrogen that, depending on the pH and solvents used in the system, may or may not be attached to the nitrogen.

For preferred methods herein, it is preferable that the hair conditioning and colour composition comprises less than about 20% surfactant, preferably less than about 10% surfactant. It is also preferable that the hair colour altering compositions comprise less than about 5% anionic surfactant.

Optional Materials

A number of additional optional materials can be added to the compositions herein described each at a level of from about 0.001% to about 5%, preferably from about 0.01% to about 3%, more preferably from about 0.05% to about 2% by weight of composition. Such materials include proteins and polypeptides and derivatives thereof; water-soluble or solubilizable preservatives such as DMDM Hydantoin, Germall 115, methyl, ethyl, propyl and butyl esters of hydroxybenzoic acid, EDTA, Euxyl (RTM) K400, natural preservatives such as benzyl alcohol, potassium sorbate and bisabalol, benzoic acid, sodium benzoate and 2-phenoxyethanol; antioxidants such as sodium sulphite, hydroquinone, sodium bisulphite, sodium metabisulphite and thyoglycolic acid, sodium dithionite, erythrobic acid and other mercaptans; dye removers such as oxalic acid, sulphated castor oil, salicylic acid and sodium thiosulphate; $H_2O_2$ stabilisers such as tin compounds such as sodium stannate, stannic hydroxide and stannous octoate, acetanilide, phenacetin colloidal silica such as magnesium silicate, oxyquinoline sulphate, sodium phosphate, and tetrasodium pyrophosphate; and ρ-hydroxybenzoates; moisturising agents such as hyaluronic acid, chitin, and starch-grafted sodium polyacrylates such as Sanwet (RTM) IM-1000, IM-1500 and IM-2500 available from Celanese Superabsorbent Materials, Portsmith, Va., USA and described in U.S. Pat. No. 4,076,663 as well as methyl cellulose, starch, higher fatty alcohols, paraffin oils, fatty acids and the like; solvents; anti-bacterial agents such as Oxeco (phenoxy isopropanol); low temperature phase modifiers such as ammonium ion sources (e.g. $NH_4Cl$); viscosity control agents such as magnesium sulfate and other electrolytes; quaternary amine compounds such as distearyl-, dilauryl-, di-hydrogenated beef tallow-, dimethyl ammonium chloride, dicetyldiethyl ammoniumethylsulphate, ditallowdimethyl ammonium methylsulphate, disoya dimethyl ammonium chloride and dicoco dimethyl ammonium chloride; enzyme stabilisers such as water soluble sources of calcium or borate species; $TiO_2$ and $TiO_2$-coated mica; perfumes and perfume solubilizers; and zeolites such as Valfour BV400 and derivatives thereof and $Ca^{2+}/Mg^{2+}$ sequestrants such as polycarboxylates, amino polycarboxylates, polyphosphonates, amino polyphosphonates etc. and water softening agents such as sodium citrate.

Method of Use

It is important that hair conditioning and colouring compositions be in a form which is easy and convenient to prepare and use by the consumer, since the oxidising agent must remain in contact with the hair for a certain period of time and not run or drip off of the hair, possibly causing eye or skin irritation. In order to provide a composition which is easy for the consumer to apply to the hair without dripping the viscosity of the composition should be controlled.

The conditioning and colouring composition may be provided as a single composition containing all the necessary conditioning and colouring ingredients. When the colouring composition comprises oxidative colouring agents and oxidising agents, it is preferably provided in the form of two components, one of which contains the oxidative colouring agent and the second of which contains the oxidising agent. The conditioning agent may be present in either of these components or as a separate third component. When the composition is provided in the form of two components these may be made up into the composition before application to the hair or applied separately to form a single composition on the hair. Percentages and amounts when discussed in this specification refer to percentages and amounts in the final composition on the hair.

Consequently the colouring and conditioning composition can be provided as a single pack or in kit form as separately packaged components to maintain stability, and, if so desired, mixed by the user immediately prior to application to the hair.

Preferably the colouring and conditioning composition is provided in the form of at least two components, a first component comprising an oxidising agent and a second component comprising a hair colouring agent. The aminofunctional polysiloxane conditioning agent may be comprised within the first or second component or may be comprised within a third component. The first and second components can either be mixed by the user immediately prior to application to the hair or can be applied separately. In one embodiment of the present invention the oxidising component comprises a stabilised cream comprising an inorganic peroxygen oxidising agent, most generally hydrogen peroxide in an amount such that the final concentration of the colouring composition as used on the hair is from about 0.05% to about 6% by weight. It may also contain additional agents as herein before described.

The first and second components and the third component if present, are separately packaged and the separate packages may be connected (e.g. as two or three chambers in a single aerosol dispenser) or may be entirely separate (e.g. two or three non-connected sachets). Preferably, they are in the form of separately packaged but associated (e.g. in attached packages) components.

When the components are packaged separately in associated packages these may be in the form of a single package having several chambers, one chamber for each separate component. A preferred pack herein is a pack having two chambers, one chamber comprising a first component comprising a hair colouring agent and a second chamber comprising a second component comprising an oxidising agent. Either or both of the first and second components may contain an aminofunctional polysiloxane, or alternatively the aminfunctional polysiloxane may be present in a third chamber. The two components can be mixed either outside the pack, for example, by hand, or within the pack, for example by a mechanical means of mixing. It is preferable that the two components are mixed sufficiently in order to provide a homogeneous hair colouring composition for application to the hair. Such a pack provides a product which is easy and convenient to use. The colouring compositions can also be packaged within blister packs and sachets. For instance, a single sachet may contain sufficient for a single application when two different sachets are mixed together. A blister pack may contain a predetermined number of the two different component compositions, each blister containing sufficient composition for one application when the two are mixed.

According to the present invention it is particularly preferred that the composition contains an oxidative colouring agent and thus according to a another aspect of the invention there is provided a method for colouring and conditioning hair comprising the steps of applying to the hair a hair colouring composition which preferably contains at least one oxidative colouring agent and at least one oxidising agent and a hair conditioning composition comprising a aminofunctional polysiloxane and subsequently rinsing the composition from the hair. The aminofunctional polysiloxane conditioner may be applied to the hair prior to the application of the hair colouring composition, at the same time as the hair colouring composition is applied or after the hair colouring composition has been applied.

Another aspect of the invention provides a kit for use in colouring and conditioning hair. This kit comprises (a) a hair colouring composition which contains at least one colouring agent and (b) a hair conditioning composition which comprises an aminofunctional polysiloxane and (c) instructions to apply the colour composition to the hair and to leave the colouring composition on the hair and then rinse the colouring composition from the hair and to apply the hair conditioning composition to the hair in a separate step.

According to another aspect of the invention a kit is provided for use in colouring and conditioning hair comprising (a) a hair colouring composition which contains at least one colouring agent and at least one oxidising agent and (b) a separately packaged hair conditioning composition which contains an aminofunctional polysiloxane conditioner. The compositions and the instructions may have any of the preferred features discussed above in the context of the method of the invention where appropriate.

The kit of the invention may comprise a series of separately packaged doses of each composition, each dose being appropriate for a single application, and the kit as a whole being sufficient to allow the consumer to carry out the method for a period.

Test Methods and Example Compositions

Particle Size Determination:

The particle size is determined according to the standard microscopy analysis method for particle size. The particle size is determined in neat (no dilution) dye product (the final dye containing product, prior to any mixing with peroxide). Within the context of this application the amino functionalised particle is clearly discernible and although there are many other features associated with other components in the dye formulation that are clearly evident in the micrograph (i.e. lamella structures associated with fatty alcohol), the amino functionalised silicones form distinct droplets that are typically clear. It is recommended, as was the case herein, that a product without the amino functionalised silicone be prepared as a placebo reference.

Sample Preparation:

A small drop of the sample product is placed on a standard microscope slide, either side of the droplet is placed two standard cover slips upon which a third cover slip is placed directly above the droplet and hence bridging the other two cover slips. Said third cover slip is then pressed down until it contacts the other two cover slips—thereby trapping product. The sample thickness is therefore guaranteed to always be the same (namely the thickness of the standard cover slip) and given this is larger than the diameter of particles reduces the chances of sample preparation affecting (deforming) the particles. The preferred sample amount is thus that defined by the volume of the void under said third cover slip (too little and the sample will not contact the underside of said third cover slip, too much and the sample will ooze from the side on compression of said third cover slip).

Particle Size Measurement:

The particle size method is typical of those known in the art, and utilizes a standard Nikon optical microscope, with standard transmitted light using ×10 objective. To aid accuracy, a Lucia G software (by Nikon) is used with the following procedure. The first step of analysis requires the user to scan and select a field that is representative of the bulk—this typically requires multiple preparations for accuracy. The observed image is transmitted via JVC video camera to a standard monitor and each particle is measured by using the standard Measure macro; namely, clicking on each side of the particle—hence measuring a diameter. To account for none spherical particles, the 'diameter' is always assessed horizontally across the monitor. By measuring in one plane, the technique automatically compensates for non spherical geometry and due to the large number of particles measured results in an equivalent average diameter. Although equivalent diameters may be determined by measuring the major and minor axes and calculating equivalent diameter via aspect ratio equations, the above technique provides equally accurate results.

Since it is typical human nature to count the largest particles first and thus to ensure that all particles are counted and measured, a small (typically using an erasable pen) dot should be placed on the monitor over each counted particle. The count procedure is continued until every single visible particle is counted within the field. In the case of a very small particle size distribution, this may result in over 400 counts. In the case of larger particle sizes, one might expect approximately 100 counts per field, however in such cases additional fields would be selected to ensure at least 200 separate particles are counted. Net, in all cases at least 200 separate particles should be measured and in all cases all particles (in practice the upper limit being 400–500) in one field are counted. On average, across all the examples sighted herein, about 300 particles would be measured per sample. Analysis can be as below (standard volume average calculated by hand to demonstrate the technique) or, more typically, using the macro. that automatically sorts the data reporting a volume average (assuming a spherical geometry based on the diameter measured above).

As with all microscope methods, this method is susceptible to error and does rely upon manual preparation of the sample between a plate and cover slip. However, multiple samples and high measurement counts, as used herein, minimize this error. Whilst other methods such as Horiba scattering techniques or Lasentec (Lasentec M100F), could be considered it has been determined that colloid and particle structures not associated with the active were a source of interference. The microscope method is limited in that particles of less than 1 micron are not discernible, however in the context of this application such particles are not preferred and further would not greatly impact volume average particle size.

Analysis Examples (Number of Observations with an Approximate Size of):

The following example bases 1 to 4 exemplify identical dye emulsion base formulations for blond shades (See dye base emulsion formula A) which have been manufactured to produce various particle sizes according to the present invention:

| Particle size (µm) | BASE 1 | BASE 2 | BASE 3 | BASE 4 |
|---|---|---|---|---|
| 1 | 31 | 124 | 6 | 0 |
| 2 | 57 | 122 | 2 | 6 |
| 3 | 30 | 90 | 62 | 20 |
| 5 | 29 | 55 | 80 | 100 |
| 7 | 13 | 16 | 44 | 63 |
| 10 | 38 | 20 | 53 | 79 |
| 15 | 31 | 4 | 18 | 22 |
| 20 | 12 | 0 | 11 | 22 |
| 25 | 4 | 0 | 5 | 1 |
| 30 | 5 | 1 | 12 | 4 |
| 35 | 1 | 0 | 7 | 0 |
| 40 | 0 | 0 | 0 | 0 |
| 45 | 0 | 0 | 0 | 0 |
| 50 | 0 | 0 | 3 | 0 |
| 60 | 0 | 0 | 0 | 0 |
| 100 | 0 | 0 | 1 | 0 |
| Total number of particles counted | 251 | 432 | 304 | 317 |
| Volume average particle size assuming sphere. | 12.48 | 5.61 | 19.65 | 11.54 |

Base 1:- One pot process
Base 2:- Oil in water process
Base 3:- One pot process
Base 4:- Phase inversion process.

The term average particle size as used herein refers to discrete amino functionalised silicones and also to discrete particles that consist of a mixture of the amino functionalised silicone and a polycation or cationic polymers—while not bound by theory such particles have been referred to as coascervates and form discrete particles consisting localised concentrations of the amino functionalised silicone that are associated with the hydrophobic environment of the polycation or cationic polymers. Examples of suitable cationic polymers include cationic cellulose (polyquaternium 10) and hydrophobically modified cationic cellulose (i.e. Amerchol's quatrisoft LM200), cationic guar (guar hydroxypropyltrimonium chloride), merquat 100 (polyquaternium 6), Merquat 550 (polyquaternium 7), Luviquat (polyquaternium-16) and Gafquat 755N (polyquaternium 11).

Treatment of Switches with Hair Care Compositions

Hair Switches

The hair switches utilised in the following test are:

Virgin light brown hair 2 g×8" Hair, (3 switches are required per test).

Water Settings

The water settings utilised for the following tests are:

Tap water, hardness 15–16 gpg.

Water flow rate 6±0.5 L/min.

Water Temperature 37±2° C.

Sample Preparation

In order to assess the performance of the present invention on hair which is regularly coloured, the hair swtich samples utilised in the test are firstly treated with a market product hair colourant (namely L'Oreal, Excellence No. 6) according to the manufacturers' instructions. Following this treatment the samples are then washed as described below 4 times.

1. Wet switch for 10 seconds.
2. Apply 0.4 ml of Prell shampoo on the hair switch, using a syringe.
3. Lather for 30 seconds using milking action, distributing shampoo on both sides of hair switch.
4. Rinse for 30 seconds.
5. Repeat steps 2,3 and 4 once.
6. Hot air dry, brushing with a vent brush, whilst blow drying on a high heat/high speed for a total of 3 minutes (1 minute on each side and 1 minute with brushing).

Initial Treatment of Sample

The switch is hung above a sink and wetted for 30 seconds with water. Excess water is squeezed out of the switch. 3.0 grams of the conditioning composition or 9.0 grams of the colouring composition to be tested is applied on the top end of the switch and spread evenly down to the bottom end, then milked into the switch. The colouring composition is then left on the switch for 30 minutes or a conditioning composition is left on the switch for 5 minutes. The switch is then rinsed with water. Excess water is squeezed out of the switch. The initial average combing index value and the initial average sensory index value are calculated by carrying out the combing test and the sensory test described herein on the wet switches.

Final Treatment of Sample

The switches are then washed as described 18 times.
1. Wet switch for 10 seconds.
2. Apply 0.4 ml of Prell shampoo on the hair switch, using a syringe.
3. Lather for 30 seconds using milking action, distributing shampoo on both sides of hair switch.
4. Rinse for 30 seconds.
5. Repeat steps 2,3 and 4 once.
6. Hot air dry, brushing with a vent brush, whilst blow drying on a high heat/high speed for a total of 3 minutes (1 minute on each side and 1 minute with brushing).
7. The final average combing index value and the final average sensory index values are calculated by carrying out the combing tests as described herein from the sample wetted again for 10 seconds.

Sensory Evaluation and Descriptive Analysis Panels

Sensory evaluation is designed to measure, analyze & interpret reactions to product characteristics as perceived by the senses of sight, smell, taste, touch and hearing. A commonly used sensory evaluation technique is descriptive analysis. Descriptive analysis is a complete, detailed and objective characterization of the sensory properties of a product using screened and qualified panelists that are specifically trained for this purpose. Descriptive analysis provides information about the perceived sensory properties (or attributes) and the strength of each sensory attribute in quantitative terms. Panelists are trained to rate the intensity of a large number of sensory properties, while ignoring personal preferences. Each sensory attribute is meticulously defined, and panelists are presented with reference materials that represent high, medium and low intensities of each sensory attribute. Panelists work in isolation in a sensory booth, and assess all sensory characteristics of one sample before moving to the next sample. Care is taken to blind and randomize the samples, and to control the environment (lighting, temperature, humidity).

A descriptive analysis panel requires 10 panelists, because the high level of training ensures a low level of variability in the data (small standard deviations). Panelists only qualify when their ratings are consistent from test-to-test, when their ratings are consistent with that of the panel, and when they are sensitive enough to discriminate small differences. Performance of descriptive analysis panels and individual panelists is monitored closely. Typically, each product is evaluated by all panelists once or twice, and the mean attribute ratings across the panelists or panelist means is calculated. Because the intensity scores are recorded in relation to a universal scale, the relative intensities among attributes and among products can be compared. Descriptive analysis ratings are used for quality control & shelf life studies, for product development, and for claim substantiation. The ASTM Guideline E 1958-98 'Standard Guide for Sensory Claim Substantiation" states that descriptive analysis data are suitable for claim substantiation if the panel shows good consistency and robustness, and when the relationship between descriptive sensory attributes and consumer responses is established.

Descriptive Analysis Panel

External Descriptive Analysis Panel at Product Perceptions

A panel consisting of 10 trained females, was used to conduct the tests.

Ease of Detangling:

Technique: With the wide end of the comb, comb 3 times to remove tangles. Assess the difficulty of removing tangles from the sample hair. If longer is needed to remove all the tangles, continue to comb with wide end until all tangles are removed.

Definition: Hard to detangle=The time and force required remove all tangles from the sample hair with the wide end of a comb, from very easy (one stroke) to very difficult (many strokes/lot of force required).

The following sensory anchors are used to define the end points of the scale:

Low Anchor=Pantene Dry/Permed/Damaged Conditioner (as available in Europe)

High Anchor=Bleached Hair as prepared using hair treated with a marketed hair bleaching product (Clairol Born Blonde) according to the manufacturer's instructions.

Ease of Combing

Technique: Once the tangles are removed, use the narrow end of the comb, and gently slide down the hair sample 3 times. Assess the amount of resistance encountered at the $3^{rd}$ combing (because some small tangles may still be removed at the first combing stroke).

Definition: Combing resistance=The force required to slide the narrow end of the comb down the length of the hair sample after removing tangles, from no resistance (no force) to very resistance (a lot of force required).

The following sensory anchors are used to define the end points of the scale:

Low Anchor=Pantene Dry/Permed/Damaged Conditioner (as available in Europe)

High Anchor=Standard conventional Styling Pomade/Styling Wax

No Coating (Dry)

Technique: After the switch is combed through, assess the visual amount of coating on the dry hair sample. Assess the amount of coating you can see on the hair (regardless of the type of coating).

Definition: Not Coated=The lack of product coating or residue seen on the hair sample (regardless of the type of coating), from very coated (low anchor) to not coated (high anchor The following sensory anchors are used to define the end points of the scale:

Low Anchor=Vaseline

High Anchor=Prell Shampoo (as available in the US)

No Residue

Technique: After the switch is combed, assess the amount of coating on the dry hair sample using a 'milking' motion with thumb and index/middle finger. Assess the amount of coating you can feel on the hair when milking.

Definition: No Residue=The lack of product coating or residue felt on the hair sample(regardless of the type of coating), from coated (low anchor) to very coated (high anchor).

The following sensory anchors are used to define the end points of the scale:

Low Anchor=Vaseline

High Anchor=Prell Shampoo (as available in the US)

Not Greasy

Technique: After the switch has been combed and assessed as outlined above for dry residue, assess the greasy feel of any residual coating on the hair using a 'milking' motion with the thumb and index/middle finger. Assess the amount of greasiness you can feel on the hair when milking.

Definition: Greasiness=The degree to which the residue on hair seems greasy in nature (as opposed to waxy, oily, stiff etc.). This attribute is specific in quantifying the amount of a specific type of coating. The scale is from very greasy (low anchor) to not greasy (high anchor).

The following sensory anchors are used to define the end points of the scale:

Low Anchor=Vaseline

High Anchor=Prell Shampoo (as available in the US)

Combing Index Values and Sensory Index Values

The combing and sensory index values are calculated according to the following formulae:

Combing Index value =

[{Erase of De-Tangling}Sample}/[{Ease of De-Tangling} Virgin +

[{Ease of Combing] Test}/[Ease of Combing] Virgin}/2

Sensory Index value = {[No Residue] Test/[No Residue] Virgin +

[Not Greasy] Test/[Not Greasy] Virgin +

[Not Coated] Test/[Not Coated] Virgin}/3

Example Compositions

The colouring composition was made up before each application by mixing the peroxide cream with the dye cream. The dye cream and the peroxide cream compositions are prepared as described herein after.

Examples of Final Dye Cream Formulations

The following dye cream formulations are to be mixed 1:1 with the peroxide cream.

| Dye Cream Formula for Dark Shades | % in use |
|---|---|
| Water | QS to 50 |
| Emulsion Base | 22.5000 |
| Dye premix | 14.0000 |
| Decyl glucoside (optional) | 0.5000 |
| 30% Aqueous Ammonium hydroxide | 4.1300 |

| Dye Cream Formula for Reds and Browns | % in use |
|---|---|
| Water | QS to 50 |
| Emulsion Base | 22.5000 |
| Dye premix | 14.0000 |
| Decyl glucoside (optional) | 0.5000 |
| 30% Aqueous Ammonium hydroxide | 5.1000 |

| Dye Cream Formula for Blondes | % in use |
|---|---|
| Water | QS to 50 |
| Emulsion Base | 22.5000 |
| Dye premix | 14.0000 |
| Decyl glucoside (optional) | 0.5000 |
| 30% Aqueous Ammonium hydroxide | 6.0000 |

Examples of Dye Emulsion Base Formulations

The following are examples of the emulsion base premix formulation

| Dye Emulsion Base Formula A | % w/w in Use |
|---|---|
| Water | As Required |
| Ceteareth 25 | 0.5400 |
| Cetyl Alcohol | 0.8100 |
| Stearyl Alcohol | 1.6300 |
| Sodium Benzoate | 0.0557 |
| Phenoxyethanol | 0.0668 |
| Benzyl Alcohol | 0.0668 |
| Steareth 2 | 0.2700 |
| Tetrasodium EDTA | 0.0223 |
| Di-PEG-2 Soyamine IPDI | 0.2115 |
| Lowenol S216 from Lowenstein | 2.1150 |
| DC Q2-8220 from Dow Corning | 1.5000 |

| Dye Emulsion Base Formula B | % w/w in Use |
|---|---|
| Water | As Required |
| Ceteareth 25 | 1.5000 |
| Cetyl Alcohol | 2.2500 |
| Stearyl Alcohol | 2.2500 |
| Sodium Benzoate | 0.0557 |
| Phenoxyethanol | 0.0668 |
| Benzyl Alcohol | 0.0668 |
| Tetrasodium EDTA | 0.0223 |
| DC Q2-8220 from Dow Corning | 2.0000 |

| Dye Emulsion Base Formula C | % w/w in Use |
|---|---|
| Water | As Required |
| Ceteareth 25 | 1.5000 |
| Cetyl Alcohol | 2.2500 |
| Stearyl Alcohol | 2.2500 |
| Sodium Benzoate | 0.0557 |
| Phenoxyethanol | 0.0668 |
| Benzyl Alcohol | 0.0668 |
| Tetrasodium EDTA | 0.0223 |
| SF1923 Fluid from General Electric | 2.0000 |

Dye Cream Emulsion Making Methods

The Dye Base Emulsions described and exemplified hereinabove can be manufactured utilising any one of the standard approaches, these include:

Oil in water process

Phase Inversion process

One-pot process

The amount of shear should be controlled to allow the desired particle size to be achieved which can be determined utilising the test method described herein.

An example Dye Base Emulsion making method is given below.

One-Pot Process for Making Dye Cream Emulsion

1. Add water to vessel. Heat to above the melt temperature of the fatty alcohols with agitation.
2. Add Fatty Alcohols and any Ethoxylated Fatty Alcohols, e.g. Ceteareth-25, Cetyl, Stearyl and Steareth-2, and allow to melt. Increase agitation.
3. If used add other surfactants such as Dihydroxyethyl Soyamine Dioleate (Lowenol S216) and/or Peg-3 Cocamine (Lowenol C243 from Lowenstein) and/or PEG-5 Cocamine (Ethomeen C/15 from Akzo Nobel).
4. Continue mixing with shear.
5. Begin cooling with shear adding preservatives at appropriate temperature.
6. During cooling add silicone containing conditioning agent with mixing. Mix until homogeneous and desired particle size achieved.
7. Cool to room temperature.

Final Dye Cream Making Method

Below is an example of how the final dye cream can be manufactured:

To the dye cream emulsion add the following:

Decyl glucoside (if used) then mix to give a homogenous product

Dye premix containing: water, anti-oxidants, solvents, precursors and couplers, then mix to give a homogenous product Ammonium hydroxide, then mix to give a homogenous final product Dye Premix Formulations:

The following is a list of typical couplers and precursors used to formulate various shade ranges.

p-Phenylenediamine
p-Aminophenol
N4,N4-bis Hydroxyethyl-p-PD sulphate
o-Aminophenol
p-Methylaminophenol
2,5,Diamonotoluene Sulphate
m-Aminophenol
4-amino-2-hydroxytoluene
Resorcinol
2-methyl resorcinol
2-Amino-3-Hydroxypyridine
2-Amino-4-Hydroxyethylaminoanisole sulphate
2-methyl-5-hydroxyethylaminophenol
m-Phenylenediamine.sulphate
1-phenyle-3-methyl-5-pyrazolone
Naphthol Additionally the dye premix formulations may comprise the following additional materials:

Water
Reducing Agents such as Sodium Sulphite
Anti-oxidants such as D and L-Ascorbic Acid
Metal Chelants such as EDTA
Solvents such as glycols and alchols Examples of Total Dye Levels used in Various Shades

| Shade | % w/w in use |
| --- | --- |
| Blondes | 0.0001 to 4.0000 |
| Reds | 0.0010 to 4.0000 |
| Browns | 0.0100 to 4.0000 |
| Blacks | 0.1000 to 4.0000 |

Dye Premix Making Method

The dye premix may be manufactured using any one of the standard approaches such as oil in water process phase inversion process one pot process An example of a dye premix manufacturing method is as follows:

1. With mixing add water to the following: solvents, anti-oxidants, precursors and couplers
2. If required warm to solubilize
3. Cool to room temperature Hydrogen Peroxide Cream Making Method Example of an Hydrogen Peroxide Emulsion Base

| Hydrogen Peroxide Emulsion Base Formula | % w/w in Formula |
| --- | --- |
| Purified Water | QS to 100 |
| Ceteareth-25 | 4.17 |
| Cetyl Alcohol | 6.25 |
| Stearyl Alcohol | 6.25 |

Hydrogen Peroxide Emulsion Base Method

The Hydrogen Peroxide Emulsion Base described herein can be made by any of the standard approaches, these include:

Oil in water process

Phase Inversion process

One-pot process

An example of a Hydrogen Peroxide Emulsion Base making method is given below.

One-pot Process for Making Hydrogen Peroxide Emulsion Base

1. Add water to vessel. With agitation heat to above the melt temperature of the fatty alcohols
2. Add Fatty Alcohols and any Ethoxylated Fatty Alcohols and allow to melt. Increase agitation.
3. Continue mixing with shear until emulsion has formed
4. Begin cooling stopping shear at appropriate temperature.

5. Cool to room temperature

Chelator Premix to Stabilise Peroxide

| | % w/w in Formula |
|---|---|
| Purified Water | QS to 15.0000 |
| Metal Chelators | 0.0010 to 1.0000% |
| Phosphoric Acid and/or Sodium Hydroxide | Adjust to pH 1–5 |

Example Making Method for Chelant Premix
1. Dissolve the chelants in the water phase
2. Adjust pH with phosphoric acid and/or sodium hydroxide as required

6% Hydrogen Peroxide Cream

| | % w/w Addition |
|---|---|
| Hydrogen Peroxide Emulsion Base | 36.00 |
| Chelator Premix | 15.00 |
| Water | QS to 100 |
| 35% Hydrogen Peroxide | 17.71 |
| pH Adjustment Gap | To pH 1–5 |

Example Making Method for 6% Hydrogen Peroxide Cream

To the Hydrogen Peroxide Emulsion Base add the following with agitation: Water, Chelant Premix and 35% Hydrogen Peroxide Solution, mix until homogeneous. Adjust pH to between one and five with appropriate amounts of phosphoric acid and/or sodium hydroxide

9% Hydrogen Peroxide Cream

| | % w/w Addition |
|---|---|
| Hydrogen Peroxide Emulsion Base | 36.00 |
| Chelator Premix | 15.00 |
| Water | QS to 100 |
| 35% Hydrogen Peroxide | 26.57 |
| pH Adjustment Gap | To pH 1–5 |

Example Making Method for 9% Hydrogen Peroxide Cream

To the Hydrogen Peroxide Emulsion Base add the following with agitation: Water, Chelant Premix and 35% Hydrogen Peroxide Solution, mix until homogeneous . Adjust pH to between one and five with appropriate amounts of phosphoric acid and/or sodium hydroxide Results:

The following table show the results for the tests carried out in order to determine the average Combing Index Value and the average Sensory Index Value for a number of compositions according to the present invention and samples of products on the market, namely L'Oreal Excellence No6 and Revlon Colorstay utilised according to the manufactures instructions. The reference sample utilised is virgin hair.

EXAMPLE 1

Hair Dye Composition According of the Present Invention

The switch samples for example 1 were treated with the dye cream for blondes containing dye emulsion base B and 9% hydrogen peroxide cream as described herein above.

EXAMPLE 2

Hair Conditioning Composition of the Present Invention

The switch samples for example 2 treated with the dye cream for blondes containing dye emulsion base B but excluding the dye premix, and excluding 9% hydrogen peroxide cream. The switches were then treated with the dye cream for blondes containing the dry emulsion B, (but excluding the aminofunctional silicones) and the 9% hydrogen peroxide cream.

Revlon Reference Example

The switch samples were treated with L'Oreal Excellence No6 but excluding the use of the L'Oreal in box conditioner and then treated with the Revlon colorstay in-box conditioner.

L'Oreal Reference Example

The switch samples were treated with L'Oreal Excellence No6 according to the manufacture's instructions including the application of the L'Oreal in-box conditioner.

| | (1) | (2) | Virgin | Revlon | L'Oreal |
|---|---|---|---|---|---|
| Initial | | | | | |
| Dry app. Coat. | 90 | 93 | 94 | 70.33 | 91 |
| Dry residue | 93 | 93 | 89 | 83.78 | 91 |
| Dry residue greasy | 98 | 98 | 98 | 89 | 94 |
| Sensory index | 1.00 | 1.01 | 1.00 | 0.87 | 0.98 |
| Final | | | | | |
| Dry app. coat | 93 | 91 | 96 | 82.67 | 91 |
| Dry residue | 94 | 93 | 91 | 82.11 | 91 |
| Dry residue greasy | 98 | 98 | 98 | 92.89 | 98 |
| Sensory index | 1.00 | 0.99 | 1.00 | 0.90 | 0.98 |
| Initial | | | | | |
| Detangling | 92 | 93 | 84 | 92.78 | 85 |
| Combing | 94 | 95 | 89 | 92.56 | 87 |
| Combing index | 1.08 | 1.09 | 1.00 | 1.07 | 0.99 |
| Final | | | | | |
| Detangling | 91 | 92 | 87 | 90.45 | 69 |
| Combing | 93 | 94 | 93 | 93.78 | 57 |
| Combing index | 1.02 | 1.03 | 1.00 | 1.02 | 0.70 |

From the table it can be clearly seen that the Example 1 and 2 formulations of the present invention provide both initial and long term sensory and combing benefits.

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair care composition comprising:
   a) an aminofunctional polysiloxane according to the formula:

wherein A represents $R_2SiO$, B represents RQSiO and C represents $R_{3-z}Q_z[A]_{x2}SiOR^1$, wherein R is an alkyl group of 1 to 5 carbons, a phenyl group, an alkoxy group or an hydroxy group and at least 50% of said R groups are methyl; $R^1$ is R or Q or $R^2$; $R^2$ is $R_{3-z}Q_z[A]_{x3}$; and Q is an amine functional group of the formula —$R^3$Z, wherein $R^3$ is a divalent alkylene radical of 3 to 6 carbons; and Z is —$N(R^4)_2$, —$NR^4(CH_2)_nN(R^4)_2$, —$N^+(R^4)_3A^-$, —$NR^4(CH_2)_n$ or $N^+(R^4)_3A^-$; wherein $R^4$ is an H atom or alkyl group of 1 to 20 carbon atoms or phenyl or benzyl; and A is $F^-$, $Cl^-$, $Br^-$, or $I^-$; and wherein t is from 0 to 3, $x_1$ is from 1 to 3000, $x_2$ is from 0 to 3000, $x_3$ is from 0 to 3000, $x_1+x_2+x_3$ is from 10 to 3000, y is from 0 to 100, z is from 0 to 1, and n is from 2 to 6; and b) anionic surfactant, wherein said anionic surfactant is present in an amount of less than 5% by weight of the composition;

c) poly cation or cationic polymer wherein said aminofunctional polysiloxane and poly cation or cationic polymer has an average effective particle size of greater than about 2 to about 50 micrometers.

2. A hair care composition according to claim 1, wherein R is a methyl, hydroxy or methoxy group and at least 50% of said R groups are methyl, $R^1$ is R or Q, Q is an amine functional group of the formula —$R^3$Z, $R^2$ is propyl or isobutyl, Z is $NH_2$ or $NHCH_2CH_2NH_2$, t is from 0 to 2, $x_1$ is from 10 to 400, $x_2$ is from 22 to 124, $x_1+x_2$ is from 10 to 400, y is from 0 to 9 when z=1, and y is from 1 to 9 when z=0.

3. A hair care composition according to claim 2, wherein R is a methyl group, $R^1$ is R, Q is $R^3$Z, t is 0, $x_2$ is from 10 to 400 and y is from 1 to 9.

4. A hair care composition according to claim 1, wherein said aminofunctional polysiloxane and polycation or cationic polymer has an average effective particle size of from about 5 to about 40 micrometers.

5. A hair care composition according to claim 1, wherein said aminofunctional polysiloxane and polycation or cationic polymer has an average effective particle size of from about 10 to about 30 micrometers.

6. A hair care composition according to claim 1, wherein said composition comprises from about 0.1% to about 10% by weight of the total composition applied to the hair of the aminofunctional polysiloxane compound.

7. A hair care composition according to claim 1, wherein said composition further comprises at least one oxidative dye.

8. A hair care composition according to claim 1, wherein said composition has a pH of from about 9 to about 11.

9. A hair care composition according to claim 1, wherein said composition further comprises at least one additional conditioning agent.

10. A hair care composition according to claim 1, wherein said aminofunctional polysiloxane has a viscosity of from about 10 cps to about 3000 cps.

11. A hair colouring and conditioning kit comprising at least two components, a first component comprising an oxidising agent and a second component comprising a hair colouring agent, wherein said kit further comprises an aminofunctional polysilixonane according to claim 1, and wherein said aminopolysiloxane is comprised within said first component, said second component or is comprised within a third component, wherein said first and said second components are mixed together immediately prior to application to the hair.

12. A packaged hair colouring and conditioning product comprising at least two chambers, a first chamber comprising a first composition comprising an oxidising agent, and a second chamber comprising a second composition comprising an oxidative hair colouring agent, wherein said package further comprises an aminofunctional polysiloxane according to claim 1, wherein said aminofunctional polysiloxane is comprised within said first composition, or said second composition.

13. A packaged hair colouring and conditioning product comprising at least three chambers, a first chamber comprising a first composition comprising an oxidising agent, a second chamber comprising a second composition comprising an oxidative hair colouring agent, and a third chamber comprising a third composition comprising a aminofunctional polysiloxane according to claim 1.

14. A method of colouring and conditioning human or animal hair comprising the steps of applying to the hair a hair colouring composition and a hair conditioning composition according to claim 1 and subsequently rinsing said hair colouring composition and said hair conditioning composition off the hair.

15. A hair colouring composition comprising at least one oxidative dye and comprising an aminofunctional polysiloxane according to the formula:

wherein A is $R_2SiO$, B is RQSiO, C is $R_{3-z}Q_z[A]_{x2}SiOR$ and R is a methyl, hydroxy or methoxy group and at least 50% of said R groups are methyl, $R^1$ is R or Q, Q is an amine functional group of the formula —$R^3$Z, $R^3$ is propyl or isobutyl, Z is $NH_2$ or $NHCH_2CH_2NH_2$—$N^+(R^4)_3A^-$, —$NR^4(CH_2)_n$ or $N^+(R^4)_3A^-$, A, is $F^-$, $Cl^-$, $Br^-$, or $I^-$, t is from 0 to 2, $x_1$ is from 10 to 400, $x_2$ is from 22 to 124, $x_1+x_2$ is from 10 to 400, y is from 0 to 9 when z=1, and y is from 1 to 9 when z=0;

b) poly cation or cationic polymer wherein said aminofunctional polysiloxane and poly cation or cationic polymer has an average effective particle size of greater than about 2 to about 50 micrometers;

such that said composition has (1) an initial average Combing Index Value on wet hair of 1 or more, as measured according to the Combing Test Method, (2) an initial average Sensory Index value of 0.95 or more as measured according to the sensory test method, (3) a final average Combing Index Value on wet hair after 18 washes as measured by the Combing Test Method of 1 or more, and (4) a final average Sensory Index value after 18 washes as measured according to the sensory test method of 0.95 or more.

16. A hair care composition according to claim 1 wherein $R^3$ is selected from the group consisting of trimethylene, pentamethylene, —$CH_2CHCH_3CH_2$—, or —$CH_2CH_2CHCH_3CH_2$—.

* * * * *